United States Patent [19]

Horwell

[11] Patent Number: 4,737,493
[45] Date of Patent: Apr. 12, 1988

[54] 7-((SUBSTITUTED)AMINO)-8-((SUBSTITUTED)CARBONYL)-METHYLAMINO)-1-OXASPIRO(4,5)DECANES AS ANALGESIC AGENTS

[75] Inventor: David C. Horwell, Foxton, England

[73] Assignee: Warner-Lambert Company, Morris Plains, N.J.

[21] Appl. No.: 870,611

[22] Filed: Jun. 9, 1986

Related U.S. Application Data

[63] Continuation-in-part of Ser. No. 750,365, Jul. 1, 1985, abandoned.

[51] Int. Cl.$^4$ .................. C07D 307/94; C07D 407/12; C07D 409/12; C07D 405/12
[52] U.S. Cl. .................................... 514/212; 514/278; 514/409; 514/462; 546/15; 540/596; 548/251; 548/407; 549/331; 549/338; 549/345
[58] Field of Search ................ 548/407, 251; 549/345; 546/15; 514/212, 278, 409, 402; 540/596

[56] References Cited

U.S. PATENT DOCUMENTS

| | | | |
|---|---|---|---|
| 4,065,573 | 12/1977 | Lednicer | 424/278 |
| 4,098,904 | 7/1978 | Szmuszkovicz | 544/400 |
| 4,145,435 | 3/1979 | Szmuszkovicz | 544/401 |
| 4,212,878 | 7/1980 | Lednicer et al. | 424/320 |
| 4,359,476 | 11/1982 | Kaplan et al. | 560/16 |
| 4,360,531 | 11/1982 | McMillan | 548/407 |
| 4,438,130 | 3/1984 | Kaplan | 546/407 |

Primary Examiner—Mark L. Bench
Attorney, Agent, or Firm—Jerry F. Janssen

[57] ABSTRACT

Substituted phenoxy-, 1-, and 2-naphthalenyloxy-, indenyl-, indolyl-, benzofuranyl-, and benzo[b]thiofuranyl-carboxamides of 7,8-(substituted-diamino)-1-oxaspiro[4.5]decanes are useful as analgesic agents.

A method of making the compounds, pharmaceutical compositions employing the compounds, and a method of alleviating pain in warm-blooded animals are also disclosed.

30 Claims, No Drawings

7-((SUBSTITUTED)AMINO)-8-((SUBSTITUTED)-CARBONYL)-METHYLAMINO)-1-OXASPIRO(4,5)-DECANES AS ANALGESIC AGENTS

CROSS-REFERENCE TO RELATED APPLICATIONS

This application is a continuation-in-part of copending application Ser. No. 750,365 filed July 1, 1985, now abandoned.

BACKGROUND OF THE INVENTION

The search for strong analgesics which also possess minimal potential for dependency has been among the highest priority efforts in pharmaceutical research. These research efforts have, to a great extent, involved chemical modifications of the opiate structure and the discovery of novel compounds which possess morphine-like activity.

The discovery of endogenous polypeptide opioids has led workers in the field to consider that these peptides, possessing less rigid liquid structures, might interact with opioid receptors other than those to which the classical rigid structure opiates, such as morphine, bind.

The concept of multiple opioid receptors has been supported by studies with nalorphine and a series of benzomorphans which display unusual pharmacological properties dissimilar from morphine, yet blocked by selective opioid antagonists. [See for example, W. R. Martin, *J. Pharmacol. Exp. Ther.*, 197: 517–532 (1976)].

The existence of multiple types of opioid receptors is of importance because of the possibility of separating desirable analgesic and psychotherapeutic effects of a drug compound from the undesirable abuse potential or habituating effects.

U.S. Pat. No. 4,145,435 describes certain 2-aminocycloaliphatic amide compounds as analgesics. In particular, trans-3,4-dichloro-N-methyl-N-[2-(1-pyrrolidinyl)cyclohexyl]benzeneacetamide has been reported to possess selective kappa opioid receptor agonist activity, and therefore to possess analgesic activity without attendant dependence liability. [See P. V. Vanvoigtlander et al., *J. Pharmacol. Exp. Ther.*, 224: 7–12 (1983)].

U.S. Pat. No. 4,098,904 discloses certain cis- and trans-N-(2-aminocycloaliphatic)benzamide compounds, for example, N-methyl-N-[2-(1-pyrrolidinyl)cyclohexyl]-3,4-dichlorobenzeneacetamide, which have potent analgesic activity, making them useful for relieving pain in warm-blooded animals.

U.S. Pat. No. 4,212,878 discloses certain N-[[1-amino-4-(substituted)cyclohexyl]methyl]benzeneacetamide compounds, for example, 2-(3,4-dichlorophenyl)-N-[[8-(1-pyrrolidinyl)-1,4-dioxaspiro[4.5]dec-8-yl]methyl]acetamide, which also possess analgesic activity with diminished dependence liability.

U.S. Pat. No. 4,360,531 discloses certain N-(2-aminocycloaliphatic)phenylacetamides and benzamides, for example trans-3,4-dichloro-N-methyl[7-(1-pyrrolidinyl)-1,4-dioxaspiro[4.5]dec-8-yl]benzamide as analgesic compounds.

U.S. Pat. No. 4,359,476 discloses certain N-(2-aminocycloaliphatic)phenylacetamides and benzamides, for example, cis- and trans-4-bromo-N-[3-methoxy-2-(1-pyrrolidinyl)cyclohexyl]-N-methylbenzamide as analgesic compounds.

U.S. Pat. No. 4,438,130 discloses certain oxaspirocyclohexylbenzeneacetamide and -benzamide compounds, for example 3,4-dichloro-N-methyl-[7-(1-pyrrolidinyl)-1-oxaspiro[4.5]dec-8-yl]benzeneacetamide, possessing analgesic activity.

SUMMARY OF THE INVENTION

The present invention provides certain oxaspiro-2-aminocyclohexylacetamides having analgesic activity and useful in the treatment of pain in warm-blooded animals.

In its broadest aspect, the present invention provides compounds of structural formula 1

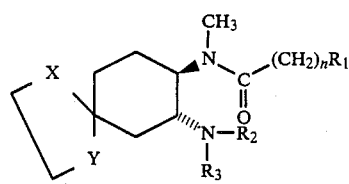

wherein n is an integer of from one to six; either of X or Y is oxygen and the other is —CH$_2$—; R$_1$ is selected from

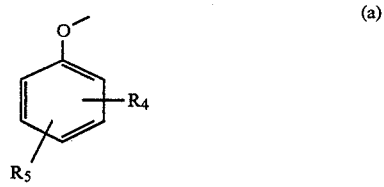

where R$_4$ and R$_5$ are independently hydrogen, fluorine, chlorine, bromine, nitro, trifluoromethyl, alkyl of from one to six carbon atoms, alkoxy of from one to six carbon atoms, or aryl;

(b) 3,4,5-trimethylphenoxy;

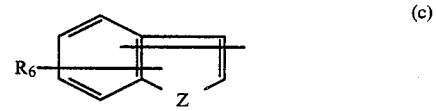

where R$_6$ is hydrogen, fluorine, chlorine, alkyl of from one to six carbon atoms, or aryl; Z is —CH$_2$—, —O—, —S—, or —NR$_7$— where R$_7$ is hydrogen, alkanoyl of from one to six carbon atoms, or alkyl of from one to six carbon atoms;

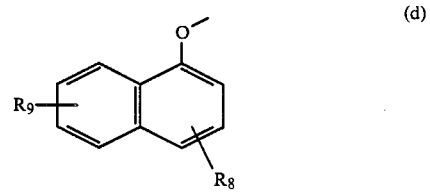

where R$_8$ and R$_9$ are independently hydrogen, fluorine, bromine, alkyl of from one to six carbon atoms, or alkoxy of from one to four carbon atoms; or

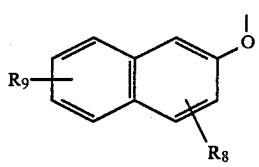

(e)

where $R_8$ and $R_9$ are as defined above; where $R_2$ is methyl and $R_3$ is hydrogen, alkyl of from one to six carbon atoms,

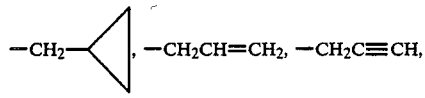

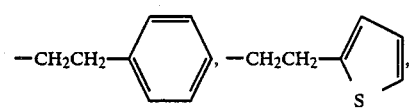

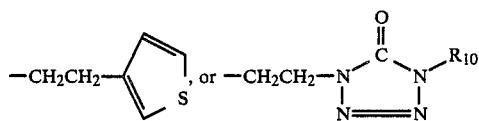

where $R_{10}$ is alkyl of from one to four carbon atoms; or where $R_2$ and $R_3$ when taken together with the nitrogen atom to which they are attached, form a pyrrolidinyl, piperidinyl, or hexahydro-1H-azepinyl ring; and the pharmaceutically acceptable acid addition salts thereof.

In another aspect, the present invention provides pharmaceutical compositions useful for the treatment of pain in a warm-blooded animal, the compositions containing an analgesically effective amount of a compound is structural formula 1 as defined above, in combination with a pharmaceutically acceptable carrier.

In accordance with yet another aspect of the present invention, there is provided a method of relieving pain in a warm-blooded animal which comprises administering to an animal in need of such treatment an analgesically effective amount of a pharmaceutical composition as defined above.

In accordance with a further aspect of the present invention, a method of preparing compounds of structural formula 1 comprises reacting an oxaspiro-trans-diamino-cyclohexane compound of structural formula 2

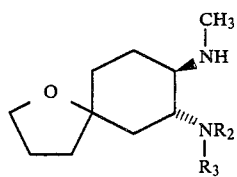

2 where $R_2$ and $R_3$ are as defined above, with a substituted carboxylic acid selected from

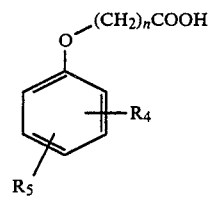

3a

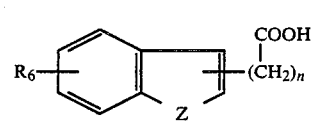

3b

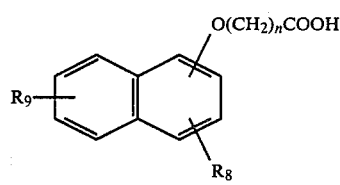

3c where n, $R_4$, $R_5$, $R_6$, $R_7$, $R_8$, $R_9$, and Z are as defined above, in the presence of a coupling reagent such as dicyclohexylcarbodiimide or carbonyldiimidazole or, alternatively reacting a compound of strucutral formula 2 with a reactive derivative of an acid of formula 3a, 3b, or 3c such as the corresponding acid chloride or acyl imidazole.

DETAILED DESCRIPTION

The compounds of the present invention consisute a class of derivatives of certain substituted oxaspirodiaminocyclohexane compounds of structure 1 above in which one nitrogen atom is an amine nitrogen substituted with methyl and a second substituent selected from the group $R_3$ as defined above, or when taken together with the nitrogen atom to which they are attached, $R_2$ and $R_3$ form a pyrrolidinyl, piperidinyl, or hexahydro-1H-azepinyl ring, and the other nitrogen atom is a N-methyl amide nitrogen further substituted with the group $R_1$ as defined above.

Compounds of the present invention contain one or more asymmetric carbon atoms and therefore exist in various stereoisomeric forms. Additionally, the compounds of this invention are capable of existing in different geometric isomeric forms. For example, the oxygen atom of the 5-membered spiro-ring may be positioned on the same side of the average plane of the cyclohexane ring as the amide nitrogen, or on the side opposite. The present invention contemplates all geometric and stereoisomeric forms of the compounds of structural formula 1 above.

The individual stereosiomers are obtained, if desired, from mixture of the different forms by known methods of resolution such as the formation of diastereomers, followed by recrystallization.

In one preferred embodiment, compounds of the present invention possess structural formua 1 above where $R_1$ is

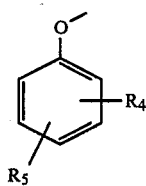

where $R_4$ and $R_5$ are independently hydrogen, fluorine, chlorine, bromine, nitro, trifluoromethyl, alkyl of from one to six carbon atoms, alkoxy of from one to six carbon atoms, or aryl.

By the term "aryl" is meant phenyl; phenyl subsituted with fluorine, chlorine, alkoxy of from one to four carbon atoms, nitro, or trifluoromethyl; 2- or 3-thienyl; and 2- or 3-thienyl substituted with alkyl of from one to four carbon atoms or alkoxy of from one to four carbon atoms.

In another preferred embodiment, compounds of te present invention possess structural formula 1 above where $R_1$ is

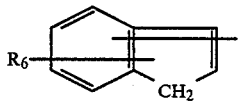

where $R_6$ is as defined above. In this embodiment, the most preferred compounds are substituted inden-1-yl compounds of formula 1 above.

In another preferred embodiment, compounds of the present invention possess structural formula 1 above where $R_1$ is

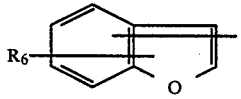

where $R_6$ is as defined above. In this embodiment, the most preferred compounds are substituted benzofuran-3-yl compounds of structural formula 1 above.

In yet another preferred embodiment, compounds of the present invention possess structural formula 1 above where $R_1$ is

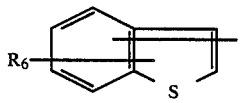

where $R_6$ is as defined above. In this embodiment, the most preferred compounds are substituted benzo[b]thiophen-4-yl compounds of formula 1 above.

In another preferred embodiment, compounds of the present invention possess structural formula 1 above where $R_1$ is

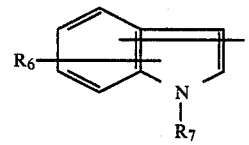

where $R_6$ and $R_7$ are as defined above. In this embodiment, the most preferred compounds are indol-3-yl compounds of structural formula 1 above.

In another preferred embodiment, compounds of the present invention possess structural formula 1 above where $R_1$ is

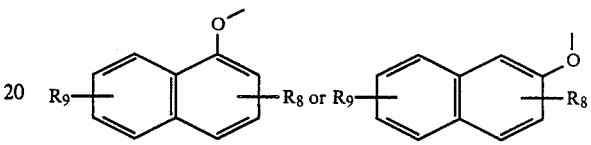

where $R_8$ and $R_9$ are independently hydrogen, fluorine, chlorine, bromine, alkyl of from one to four carbon atoms or alkoxy of from one to four carbon atoms.

Preferred substituents for $R_2$ and $R_3$ are those where $R_2$ is methyl and $R_3$ is lower alkyl, most preferred methyl, or where $R_2$ and $R_3$ taken together with the nitrogen atom to which they are atached form a pyrrolidinyl ring.

Compounds of the present invention are exemplified by the following:

[5R-(5α,7α,8β)]-N-Methyl-N-[7-(methyl-2-propynylamino)-1-oxaspiro[4.5]dec-8-yl]phenoxyacetamide.

[5S-(5α,7α,8β)]-N-Methyl-N-[7-(methyl-2-propynylamino)-1-oxaspiro[4.5]dec-8-yl]phenoxyacetamide.

[5R-(5α,7β,8α)-N-Methyl-N-[7-(methyl-2-propynylzamino)-1-oxaspiro[4.5]dec-8-yl]phenoxyacetamide.

[5S-(5α,7β,8α)]-N-Methyl-N-[7-(methyl-2-propynylamino)-1-oxaspiro[4.5]dec-8-yl]phenoxyacetamide.

[5R-(5α,7α,8β)]-2-(4-Fluorophenoxy)-N-[7-(1-pyrrolidinyl)amino]-1-oxaspiro[4.5]dec-8-yl]acetamide.

[5S-(5α,7α,8β)]-2-(4-Fluorophenoxy)-N-[7-(1-pyrrolidinyl)amino]-1-oxaspiro[4.5]dec-8-yl]acetamide.

[5R-(5α,7β,8α)]-2-(4-Fluorophenoxy)-N-[7-(1-pyrrolidinyl)amino]-1-oxaspiro[4.5]dec-8-yl]acetamide.

[5S-(5α,7β,8α)]-2-(4-Fluorophenoxy)-N-[7-(1-pyrrolidinyl)amino]-1-oxaspiro[4.5]dec-8-yl]acetamide.

[5R-(5α,7α,8β)]-2-(4-Fluorophenoxy)-N-[7-[methyl(2-phenylethyl)amino]-1-oxaspiro[4.5]dec-8-yl]acetamide.

[5S-(5α,7α,8β)]-2-(4-Fluorophenoxy)-N-[7-[methyl(2-phenylethyl)amino]-1-oxaspiro[4.5]dec-8-yl]acetamide.

[5R-(5α,7β,8α)]-2-(4-Fluorophenoxy)-N-[7-[methyl(2-phenylethyl)amino]-1-oxaspiro[4.5]dec-8-yl]acetamide.

[5S-(5α,7β,8α)]-2-(4-Fluorophenoxy)-N-[7-[methyl(2-phenylethyl)amino]-1-oxaspiro[4.5]dec-8-yl]acetamide.

[5R-(5α,7α,8β)]-N-Methyl-N-[7-(1pyrrolidinyl)-1-oxaspiro[4.5]dec-8yl]-2-(3-nitrophenoxy)acetamide.

[5S-(5α,7α,8β)]-N-Methyl-N-[7-(1-pyrrolidinyl)-1-oxaspiro[4.5]dec-8-yl]-2-(3-nitrophenoxy)acetamide.

[5R-(5α,7β,8α)]-N-Methyl-N-[7-(1-pyrrolidinyl)-1-oxaspiro[4.5]dec-8-yl]-2-(3-nitrophenoxy)acetamide.

[5S-(5α,7β,8α)]-N-Methyl-N-[7-(1-pyrrolidinyl)-1-oxaspiro[4.5]dec-8yl]-2-(3-nitrophenoxy)acetamide.

[5R-(5α,7α,8β)]-N-Methyl-N-[7-(1-pyrrolidinyl)-1-oxaspiro[4.5]dec-8-yl]-2-(3-trifluoromethylphenoxy)acetamide.

[5S-(5α,7α,8β)]-N-Methyl-N-[7-(1-pyrrolidinyl)-1-oxaspiro[4.5]dec-8-yl]-2-(3-trifluoromethylphenoxy)acetamide.

[5R-(5α,7β,8α)]-N-Methyl-N-[7-(1-pyrrolidinyl)-1-oxaspiro[4.5]dec-8-yl]-2-(3-trifluoromethylphenoxy)acetamide.

[5S-(5α,7β,8α)]-N-Methyl-N-[7-(1-pyrrolidinyl)-1-oxaspiro[4.5]dec-8-yl]-2-(3-trifluoromethylphenoxy)acetamide.

[5R-(5α,7α,8β)]-2-(3,4-Dichlorophenoxy)-N-methyl[7-(1-pyrrolidinyl)-1-oxaspiro[4.5]dec-8-yl]acetamide.

[5S-(5α,7α,8β)]-2-(3,4-Dichlorophenoxy)-N-methyl[7-(1-pyrrolidinyl)-1-oxaspiro[4.5]dec-8-yl]acetamide.

[5-R-(5α,7β,8α)]-2-(3,4-Dichlorophenoxy)-N-methyl[7-(1-pyrrolidinyl)-1-oxaspiro[4.5]dec-8-yl]acetamide.

[5S-(5α,7β,8α)]-2-(3,4-Dichlorophenoxy)-N-methyl[7-(1-pyrrolidinyl)-1-oxaspiro[4.5]dec-8-yl]acetamide.

[5R-(5α,7α,8β)]-2-(2,6-Dichlorophenoxy)-N-methyl[7-(1-pyrrolidinyl)-1-oxaspiro[4.5]dec-8-yl]acetamide.

[5S-(5α,7α,8β)]-2-(2,6-Dichlorophenoxy)-N-methyl[7-(1-pyrrolidinyl)-1-oxaspiro[4.5]dec-8-yl]acetamide.

[5R-(5α,7β,8α)]-2-(2,6-Dichlorophenoxy)-N-methyl[7-(1-pyrrolidinyl)-1-oxaspiro[4.5]dec-8-yl]acetamide.

[5S-(5α,7β,8α)]-2-(2,6-Dichlorophenoxy)-N-methyl[7-(1-pyrrolidinyl)-1-oxaspiro[4.5]dec-8-yl]acetamide.

[5R-(5α,7α,8β)]-2-(3,5-Dichlorophenoxy)-N-methyl[7-(1-pyrrolidinyl)-1-oxaspiro[4.5]dec-8-yl]acetamide.

[5S-(5α,7α,8β)]-2-(3,5-Dichlorophenoxy)-N-methyl[7-(1-pyrrolidinyl)-1-oxaspiro[4.5]dec-8-yl]acetamide.

[5R-(5α,7β,8α)]-2-(3,5-Dichlorophenoxy)-N-methyl[7-(1-pyrrolidinyl)-1-oxaspiro[4.5]dec-8-yl]acetamide.

[5S-(5α,7β,8α)]-2-(3,5-Dichlorophenoxy)-N-methyl[7-(1-pyrrolidinyl)-1-oxaspiro[4.5]dec-8-yl]acetamide.

[5R-(5α,7α,8β)]-N-Methyl-2-(1-naphthalenyloxy)-N-[7-(1-pyrrolidinyl)-1-oxaspiro[4.5]dec-8-yl]acetamide.

[5S-(5α,7α,8β)-N-Methyl-2-(1-naphthalenyloxy)-N-[7-(1-pyrrolidinyl)-1-oxaspiro[4.5]dec-8-yl]acetamide.

[5R-(5α,7β,8α)]-N-Methyl-2-(1-naphthalenyloxy)-N-[7-(1-pyrrolidinyl)-1-oxaspiro[4.5]dec-8-yl]acetamide.

[5S-(5α,7β,8α)-N-Methyl-2-(1-naphthalenyloxy)-N-[7-(1-pyrrolidinyl)-1-oxaspiro[4.5]dec-8-yl]acetamide.

[5R-(5α,7α,8β)]-N-Methyl-2-(1-naphthalenyloxy)-N-[7-(1-pyrrolidinyl)-1-oxaspiro[4.5]dec-8-yl]acetamide.

[5S-(5α,7α,8β)]-N-Methyl-2-(1-naphthalenyloxy)-N-[7-(1-pyrrolidinyl)-1-oxaspiro[4.5]dec-8-yl]acetamide.

[5R-(5α,7β,8α)]-N-Methyl-2-(1-naphthalenyloxy)-N-[7-(1-pyrrolidinyl)-1-oxaspiro[4.5]dec-8-yl]acetamide.

[5S-(5α,7β,8α)]-N-Methyl-2-(1-naphthalenyloxy)-N-[7-(1-pyrrolidinyl)-1-oxaspiro[4.5]dec-8-yl]acetamide.

[5R-(5α,7α,8β)]-N-Methyl-N-[7-[methyl[2-(2-thienyl)ethyl]amino]-1-oxaspiro[4.5]dec-8-yl]-2-(1-naphthalenyloxy)acetamide.

[5S-(5α,7α,8β)]-N-Methyl-N-[7-[methyl[2-(2-thienyl)ethyl]amino]-1-oxaspiro[4.5]dec-8-yl]-2-(1-naphthalenyloxy)acetamide.

[5R-(5α,7β,8α)]-N-Methyl-N-[7-[methyl[2-(2-thienyl)ethyl]amino]-1-oxaspiro[4.5]dec-8-yl]-2-(1-naphthalenyloxy)acetamide.

[5S-(5α,7β,8α)]-N-Methyl-N-[7-[methyl[2-(2-thienyl)ethyl]amino]-1-oxaspiro[4.5]dec-8-yl]-2-(1-naphthalenyloxy)acetamide.

[5R-(5α,7α,8β)]-N-Methyl-N-[7-(methyl-2-propenylamino)-1-oxaspiro[4.5]dec-8-yl]-1H-indene-3-acetamide.

[5S-(5α,7α,8β)]-N-Methyl-N-[7-(methyl-2-propenylamino)-1-oxaspiro[4.5]dec-8-yl]-1H-indene-3-acetamide.

[5R-(5α,7β,8α)]-N-Methyl-N-[7-(methyl-2-propenylamino)-1-oxaspiro[4.5]dec-8-yl]-1H-indene-3-acetamide.

[5S-(5α,7β,8α)]-N-Methyl-N-[7-(methyl-2-propenylamino)-1-oxaspiro[4.5]dec-8-yl]-1H-indene-3-acetamide.

[5R-(5α,7α,8β)]-N-Methyl-[7-(1-pyrrolidinyl)-1-oxaspiro[4.5]dec-8-yl]-3-indeneacetamide.

[5-S-(5α,7α,8β)-N-Methyl-[7-(1-pyrrolidinyl)-1-oxaspiro[4.5]dec-8-yl]-3-indeneacetamide.

[5R-(5α,7β,8α)]-N-Methyl-[7-(1-pyrrolidinyl)-1-oxaspiro[4.5]dec-8-yl]-3-indeneacetamide.

[5S-(5α,7β,8α)]-N-Methyl-[7-(1-pyrrolidinyl)-1-oxaspiro[4.5]dec-8-yl]-3-indeneacetamide.

[5R-(5α,7α,8β)]-N-[7-Dimethylamino)-1-oxaspiro[4,5]-dec-8-yl]-N-methyl-1H-indole-3-acetamide.

[5S-(5α,7α,8β)]-N-[7-(Dimethylamino)-1-oxaspiro[4.5]-dec-8-yl]-N-methyl-1H-indole-3-acetamide.

[5R-(5α,7β,8α)]-N-[7-(Dimethylamino)-1-oxaspiro[4.5]-dec-8-yl]-N-methyl-1H-indole-3-acetamide.

[5S-(5α,7β,8α)]-N-[7-(Dimethylamino)-1-oxaspiro[4.5]-dec-8-yl]-N-methyl-1H-indole-3-acetamide.

[5R-(5α,7α,8β)]-N-Methyl-[7-(1-pyrrolidinyl)-1-oxaspiro[4.5]dec-8-yl]-3-indoleacetamide.

[5S-(5α,7α,8β)]-N-Methyl-[7-(1-pyrrolidinyl)-1-oxaspiro[4.5]dec-8-yl]-3-indoleacetamide.

[5R-(5α,7β,8α)]-N-Methyl-[7-(1-pyrrolidinyl)-1-oxaspiro[4.5]dec-8-yl]-3-indoleacetamide.

[5S-(5α,7β,8α)]-N-Methyl-[7-(1-pyrrolidinyl)-1-oxaspiro[4.5]dec-8-yl]-3-indoleacetamide.

[5R-(5α,7α,8β)]-N-Methyl-[7-(1-pyrrolidinyl)-1-oxaspiro[4.5]dec-8-yl]-2-benzo[b]furanacetamide.

[5S-(5α,7α,8β)-N-Methyl-[7-(1-pyrrolidinyl)-1-oxaspiro[4.5dec-8-yl]-2-benzo[b]furanacetamide.

[5R-(5α,7β,8α)]-N-Methyl-[7-(1-pyrrolidinyl)-1-oxaspiro[4.5]dec-8-yl]-2-benzo[b]furanacetamide.

[5S-(5α,7β,8α)]-N-Methyl-[7-(1-pyrrolidinyl)-1-oxaspiro[4.5]dec-8-yl]-2-benzo[b]furanacetamide.

[5R-(5α,7α,8β)]-N-Methyl-[7-(1-pyrrolidinyl)-1-oxaspiro[4.5]dec-8-yl]-3-benzo[b]furanacetamide.

[4S-(5α,7α,8β)-N-Methyl-[7-(1-pyrrolidinyl)-1-oxaspiro[4.5]dec-8-yl]-3-benzo[b]furanacetamide.

[5R-(5α,7β,8α)]-N-Methyl-[7-(1-pyrrolidinyl)-1-oxaspiro[4.5]dec-8-yl]-3-benzo[b]furanacetamide.

[5S-(5α,7β,8α)]-N-Methyl-[7-(1-pyrrolidinyl)-1-oxaspiro[4.5]dec-8-yl]-3-benzo[b]furanacetamide.

[5R-(5α,7α,8β)]-N-Methyl-[7-(1-pyrrolidinyl)-1-oxaspiro[4.5]dec-8-yl]-4-benzo[b]furanacetamide.

[5S-(5α,7α,8β)]-N-Methyl-[7-(1-pyrrolidinyl)-1-oxaspiro[4.5]dec-8-yl]-4-benzo[b]furanacetamide.

[5R-(5α,7α,8α)]-N-Methyl-[7-(1-pyrrolidinyl)-1-oxaspiro[4.5]dec-8-yl]-4-benzo[b]furanacetamide.

[5S-(5α,7α,8α)]-Methyl-[7-(1-pyrrolidinyl)-1-oxaspiro[4.5]dec-8-yl]-4-benzo[b]furanacetamide.

[5R-(5α,7α,8β)]-N-[7-[(Cyclopropylmethyl)methylamino]-1-oxaspiro[4.5]dec-8-yl]-N,2-dimethyl-3-benzo[b]furanacetamide.

[5S-(5α,7α,8β)]-N-[7-[(Cyclopropylmethyl)methylamino]-1-oxaspiro[4.5]dec-8-yl]-N,2-dimethyl-3-benzo[b]furanacetamide.

[5R-(5α,7β,8α)]-N-[7-[(Cyclopropylmethyl)methylamino]-1-oxaspiro[4.5]dec-8-yl]-N,2-dimethyl-3-benzo[b]furanacetamide.

[5S-(5α,7β,8α)]-N-[7-[(Cyclopropylmethyl)methylamino]-1-oxaspiro[4.5]dec-8-yl]-N,2-dimethyl-3-benzo[b]furanacetamide.

Compounds of the present invention are prepared by reactions in which an oxaspiro-diaminocyclohexane of structural formula 2

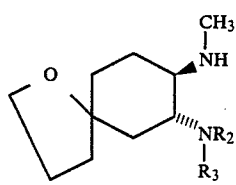

where $R_2$ and $R_3$ are as defined above is coupled with the desired carboxylic acid or reactive derivative thereof such as the corresponding acid chloride or acyl imidazole.

The appropriate carboxylic acid may be reacted directly with the diamine 2 in the presence of a coupling reagent such as dicyclohexylcarbodiimide, carbonyldiimidazole or the like. The reaction is generally carried out in a suitable solvent such as tetrahydrofuran or dioxane at ambient temperature but, depending upon the reactivity of the specific starting material employed, the reaction time, solvent employed, and reaction temperature may be varied. Reaction temperatures between −25° C. and the boiling point of the solvent may be employed.

The reaction between the acid chloride and diamine 2 is generally carried out at ambient temperature in a suitable solvent such as chloroform or dichloromethane in the presence of an acid acceptor such as a tertiary amine or an alkali or alkaline earth carbonate or bicarbonate. The mixture of amine 2 and acid halide is allowed to stand until the reaction is complete as indicated by chromatographic analysis of the reaction mixture.

Alternatively, the desired starting carboxylic acid may first be converted to the corresponding acyl imidazole compound by conventional methods and the acyl imidazole then reacted with the diamine compound, 2, in the conventional manner.

In a further alternative method, the desired carboxylic acid (or reactive derivative thereof) is reacted with the oxaspiro-diaminocyclohexane 2 where $R_2$ is methyl and $R_3$ is hydrogen to form the corresponding amide intermediate. This intermediate is then further reacted with a reactive alkyl, alkenyl, alkynyl or cycloalkyl halide such as allylchloride or bromide, propargyl chloride or bromide, or cyclopropylmethyl chloride or bromide and the like to form the compounds where $R_3$ is allyl, propargyl, or cyclopropylmethyl.

The desired product of any of the foregoing methods is recovered from the reaction mixture by well known techniques. For example, the crude reaction mixture may be concentrated under vacuum, if desired, to remove the solvent and other volatile components of the reaction mixture to yield the product, usually as an oil. This residual material may be further purified by dissolving it in a solvent such as diethyl ether and the resulting solution washed with water. The organic layer from this washing is separated, dried and evaporated to yield the product as an oil or crystalline solid which may then be recrystallized to obtain the pure material.

The starting carboxylic acids are known, or if novel, are prepared by reaction methods well known in the art and, for the most part, analogous to methods employed in the synthesis of known carboxylic acids of the same type.

Acid chlorides of the starting carboxylic acids are prepared by reaction of the acid compounds with, for example, thionyl chloride, phophoryl chloride, or the like.

The acyl imidazole derivatives of the carboxylic acids are prepared by reaction carbonyldiimidazole with the appropriate acid in the convention manner.

The starting oxaspiro-diaminocyclohexanes of formula 2 are prepared by the reactions shown in Reaction Sequence I. The conversion of compound 5 to compound 13 is carried out by reactions detailed in U.S. Pat. No. 4,438,130 which is incorporated herein by reference.

1,4-Cyclohexanedione, (compound 4, Aldrich Chemical Co., Milwaukee, WI, U.S.A.) is converted to 8-oxo-1,4-dioxaspiro[4.5]decane, 5, by the method described by K. C. Nicolaou, *J. Am. Chem. Soc.*, 102 (4): 1404–1409 (1980).

REACTION SEQUENCE I

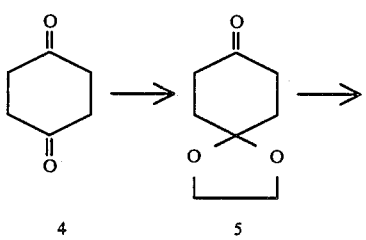

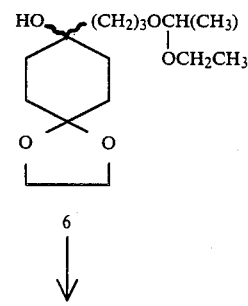

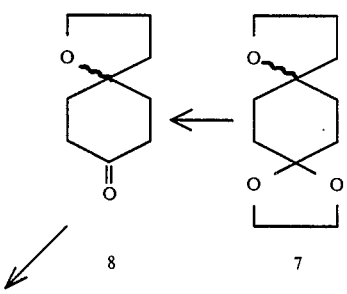

-continued
REACTION SEQUENCE I

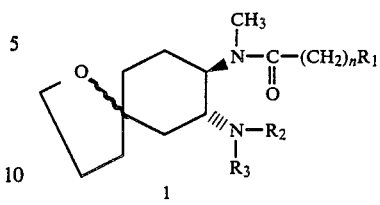

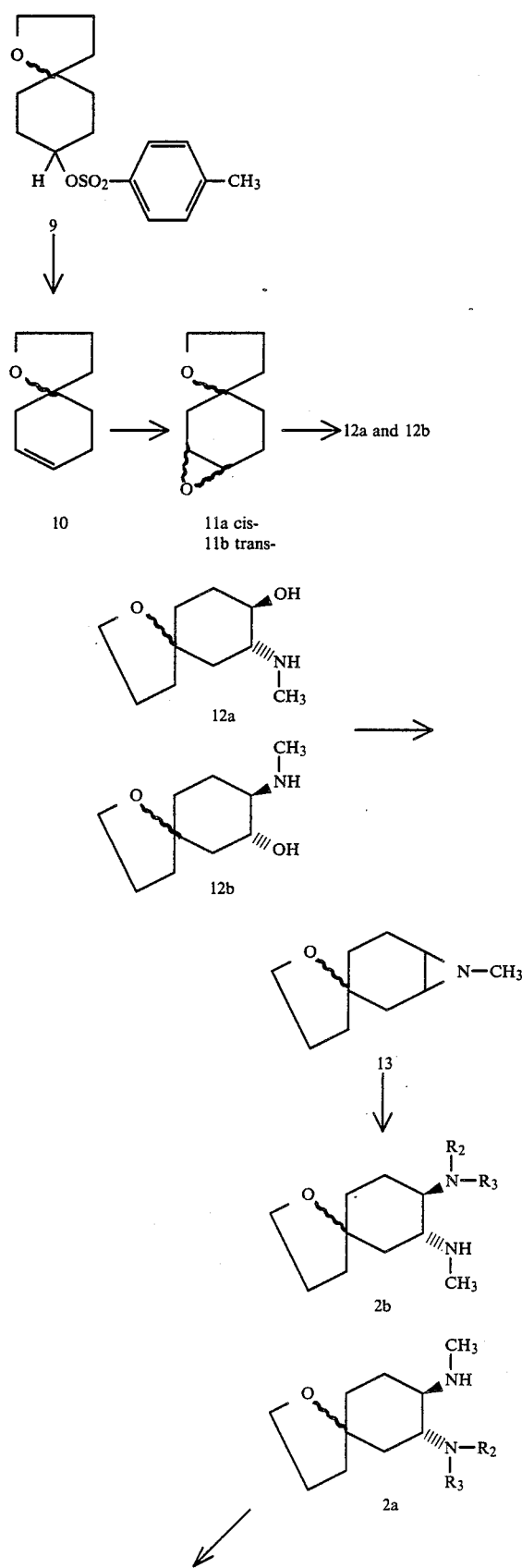

Compound 5 is reacted with lithium and ethyl-3-bromopropyl acetaldehyde acetal (*J. Org. Chem.*, 37: 1947 (1972)) in diethyl ether to produce 8-[3-(1-ethoxy)-propyl]-1,4-dioxaspiro[4.5]decan-8-ol, 6.

Compound 6 is cleaved by the action of an acid resin to produce the dioxaspiro-diol intermediate 8-(2-hydroxyethyl)-1,4-dioxaspiro[4.5]decan-8-ol which is converted without further purification to trioxaspiro[4.2.4]tetradecane, 7, by the action of triethylamine and methanesulfonyl chloride in methylene chloride.

Compound 7 is treated with perchloric acid for eighteen hours to cleave the ethylene ketal functionality and to produce 1-oxaspiro[4.5]decan-8-one, 8.

Reduction of the ketone function of compound 8 with lithium aluminum hydride in diethyl ether followed by reaction with p-toluenesulfonyl chloride produces 1-oxaspiro[4.5]decan-8-ol, 4-methylbenzenesulfonate, 9.

Compound 9 is converted to the unsaturated spiro compound 1-oxaspiro[4.5]dec-7-ene, 10, by treatment of 9 with 1,8-diazabicyclo[5.4.0]undec-5-ene.

Oxidation of the carbon-carbon double bond of compound 10 by the action of m-chloroperbenzoic acid produces a mixture of the isomers cis-($\pm$)-1'$\alpha$,3'$\beta$,6'$\alpha$)-dihydrospiro[furan-1(3H),3'-[7]-oxabicyclo[4.1.0]-heptane, 11a, and trans-($\pm$)-1'$\alpha$,3'$\beta$,6'$\alpha$)-dihydrospiro[furan-1(3H),3'-[7]-oxabicyclo[4.1.0]-heptane, 11b.

The mixture of isomers 11a and 11b is further converted without separation to a mixture of 7-(methylamino)-1-oxaspiro[4.5]decan-8-ol, 12a, and 8-(methylamino)-1-oxaspiro[4.5]decan-7-ol, 12b, by heating the mixture of 11a and 11b under reflux with methylamine in the presence of a small amount of water for a period of about 10 to 24 hours.

The mixture of compounds 12a and 12b is not separated, but is converted to 4',5'-dihydro-7-methylspiro[7-azabicyclo[4.1.0]heptane-3,2'(3'H)-furan], 13, by treatment with chlorosulfonic acid in diethyl ether at temperatures between about $-10°$ C. and $5°$ C.

The oxaspiro-aza-bicyclo compound, 13, is converted to the desired intermediate, 2a, (together with the unwanted isomer, 2b) by heating 13 with the appropriate amine under reflux in the presence of water and, optionally, ammonium chloride for a period of from about 10 to 24 hours, generally from about 18 to 20 hours. The mixture of isomeric oxaspiro cyclohexanediamines, 2a and 2b is separated by convention techniques, and compound 2a is employed in the preparation of the compounds of the present invention.

Compound 2a is reacted with the desired carboxylic acid in the presence of a coupling reagent such as carbonyldiimidazole or dicyclohexylcarbodiimide as described above or, alternatively, with the desired acid chloride or acyl imidazole to produce the compounds of the present invention, 1.

The free base form of the compounds of this invention are converted, if desired, by known methods to the corresponding acid addition salts. Suitable acids useful for this purposes include hydrochloric, hydrobromic, hydriodic, sulfuric, nitric, phosphoric, acetic, benzoic, citric, maleic, tartaric, succinic, gluconic, ascorbic, sulfamic, oxalic, pamoic, methanesulfonic, benzenesulfonic, or mixtures thereof.

The salts are produced by contacting the free base form of the compounds of this invention with an equivalent amount of the desired acid in a suitable solvent such as water, an alcohol, or aqueous alcohol. The solvent is removed to yield the salt which may be used as such or further purified by recrystallization. In the particular cases where the compounds of this invention are made by reacting an oxaspirocyclohexanediamine with an acid chloride, the product of the reaction is the hydrochloride salt of the desired compound which may be employed as the analgesic agent, or may be converted, if desired, to other salts by first converting to the free base.

The free base form of compounds of the present invention may be regenerated from the salts, if desired, by contacting the salt with an aqueous solution of a base such as sodium hydroxide, potassium carbonate, sodium bicarbonate, ammonia, and the like.

The free base form of compounds of this invention and their corresponding acid addition salts differ in such physical characteristics as melting point and solubility in polar solvents such as water, but are otherwise considered equivalent for the purposes of this invention.

The compounds of the present invention possess significant analgesic activity with the potential for minimum dependence liability due to their selective kappa opioid receptor binding properties. In addition to acting as analgesics, selective kappa opioid agonists also cause opioid receptor-mediated sedation, diuresis, and corticosteroid elevations. Accordingly, the compounds of the present invention may also be useful diuretics and psychotherapeutic agents as well as analgesics.

Representative examples of the compounds of this invention have shown activity in standard laboratory analgesic tests such as the rat paw pressure test as shown by the data appearing in Table 1.

Moreover, representative examples of compounds of the present invention when tested in vitro to determine the extent of opioid receptor binding were found to be selectively bound to the kappa opioid receptors with much lower binding to the mu opioid receptor sites. The benefits of this selectivity in binding to opioid receptor binding sites has been discussed above and is also described in M. B. Tyers, *Br. J. Pharmacol.,* (1980) 69: 503–512.

Measurement of the kappa opioid receptor binding activity of compounds of the present invention was made by the following method. Guinea pig brain homogenates were prepared fresh daily utilizing the method of Gillan et al. *Br. J. Pharmacol.,* (1980) 70: 481–490.

The binding of tritiated etorphine to brain homogenates was measured in the presence unlabeled competitor compounds of the present invention with 200 nanomolar D-alanine-D-leucine-enkephalin (acronym DADLE) and 200 nanomolar D-ala-MePheGly-ol-enkephalin (acronym DAGO) added to saturate the delta and mu opioid receptors, respectively. The reaction was terminated by rapid filtration and the radioactivity bound to the filters counted by liquid scintillation spectrophotometry.

Measurement of the mu and delta opioid receptor binding activity of the compounds of this invention was made by the following method. Guinea pig brain homogenates were freshly prepared daily by the method of Gillan et., cited above.

Homogenates were incubated for 150 minutes at 0° C. with either tritiated DAGO to measure mu receptor binding activity, or with tritiated DADLE in the presence of a ten-fold excess of unlabeled DAGO to measure delta opioid receptor binding. Nonspecific binding was determined in the presence of $10^{-6}$ molar DAGO and $10^{-6}$ molar DADLE.

Reactions were terminated by rapid filtration and the radioactivity bound to the filters counted by liquid scintillation spectrophotometry.

The data were analyzed by the methods of Scatchard, *Ann. N.Y. Acad. Sci.*, 51: 660–672 (1949) and Hill, *J. Physiol.*, 40: IV–VIII (1910). The inhibition of the binding of tritiated etorphine, DAGO and DADLE by cold ligands was determined from the regression of log percentage inhibition of specific binding or log concentration of cold ligand. The inhibition constant, $K_i$, was calculated from the equation:

$$K_i = \frac{IC_{50}}{1 + [L]/K_D}$$

where [L] is the concentration of the labeled ligand and $K_D$ is the equilibrium dissociation constant.

The results of these tests are presented in Table I.

TABLE I

| Compound | Receptor Binding ($K_i$ moles/liter) | | Rat Paw Pressure (MPE$_{50}$ I.V.) Mg/kg |
|---|---|---|---|
| | Kappa | Mu | |
| N—Methyl-N—[7-(1-pyrrolidinyl)-1-oxaspiro[4.5]-dec-8-yl]-2-benzo[b]thiophene-acetamide | $1.75 \times 10^{-9}$ | $8.62 \times 10^{-8}$ (Ratio of kappa/mu binding = 49) | 0.03 |
| N—Methyl-N—[7-(1-pyrrolidinyl)-1-oxaspiro[4.5]-dec-8-yl]-4-benzo[b]thiophene-acetamide | $2.97 \times 10^{-9}$ | $4.84 \times 10^{-7}$ (Ratio of kappa/mu binding = 163) | 0.02 |

The compounds of the present invention and/or their non-toxic, pharmaceutically acceptable acid adition salts may be administered to mammals in pharmaceutical compositions which comprise one or more compounds of this invention and/or salts thereof in combination with a pharmaceutically acceptable non-toxic carrier.

As parenteral compositions, the compounds of this invention may be administered with conventional injectable liquid carriers such as sterile, pyrogen-free water, sterile peroxide-free ethyl oleate, dehydrated alcohols, polypropylene glycol, and mixtures thereof.

Suitable pharmaceutical adjuvants for the injectable solutions include stabilizing agents, solubilizing agents, buffers, and viscosity regulators. Examples of these adjuvants include ethanol, ethylenediamine tetraacetic acid (EDTA), tartrate buffers, citrate buffers, and high molecular weight polyethylene oxide viscosity regulators. These pharmaceutical formulations may be injected intramuscularly, intraperitoneally, or intravenously.

As solid or liquid pharmaceutical compositions, the compounds of the present invention may be administered to mammals orally in combination with conventional compatible carriers in solid or liquid form. These orally administered pharmaceutical compositions may contain conventional ingredients such as binding agents such as syrups, acacia, gelatin, sorbitol, tragacanth, polyvinylpyrrolidone, and mixtures thereof.

The compositions may further include fillers such as lactose, mannitol, starch, calcium phosphate, sorbitol, methylcellulose, and mixtures thereof.

These oral compositions may also contain lubricants such as magnesium stearate, high molecular weight polymers such as polyethylene glycol, high molecular weight fatty acids such as stearic acid, silica, or agents to facilitate disintegration of the solid formulation such as starch, and wetting agents such as sodium lauryl sulfate.

The oral pharmaceutical compositions may take any convenient form such as tablets, capsules, lozenges, aqueous or oily suspensions, emulsions, or even dry powders which may be reconstituted with water or other suitable liquids prior to use.

The solid or liquid forms may contain flavorants, sweeteners, and/or preservatives such as alkyl p-hydroxybenzoates. The liquid forms may further contain suspending agents such as sorbitol, glucose, or other sugar syrups, methyl-, hydroxymethyl-, or carboxymethylcellulose, and gelatin, emulsifying agents such as lecithin or sorbitol monooleate, and conventional thickening agents. The liquid compositions may be encapsulated in, for example, gelatin capsules.

As topically administered pharmaceutical compositions, the compounds of the present invention may be administered in the form of ointments or creams containing from about 0.1% to about 10% by weight of the active component in a pharmaceutical ointment or cream base.

Compounds of the present invention may be rectally administered in the form of suppositories. For preparing suppositories, a low-melting wax such as a mixture of fatty acid glycerides or cocoa butter is first melted and the active ingredient is dispersed homogenously in the melt. The mixture is then poured into convenient sized molds and allowed to cool and solidify.

Preferably the pharmaceutical compositions of this invention are in unit dosage form. In such form, the preparation is subdivided into unit doses containing appropriate amounts of the active component. The unit dosage can be a packaged preparation with the package containing discrete quantities of the preparation. For example, the package may take the form of packaged tablets, capsules, and powders in envelopes, vials or ampoules. The unit dosage form can also be a capsule, cachet, or tablet itself or can be the appropriate number of any of these packaged forms.

The quantity of active compound in the unit dosage form may be varied or adjusted from about 0.5 mg to about 350 mg according to the particular application and the potency of the active ingredient.

When employed systematically in therapeutic use as analgesic agents in the pharmaceutical method of this invention, the compounds are administered at doses of from about 0.05 mg to about 2.0 mg of active compound per kilogram of body weight of the recipient.

The following specific preparative examples are provided to enable one skilled in the art to practice the present invention. These examples are not to be read as limiting the scope of the invention as defined by the appended claims, but merely as illustrative thereof.

EXAMPLE 1

Preparation of
2-(3,4-Dichlorophenoxy)-N-methyl-[7-(1-pyrrolidinyl)-1-oxaspiro[4.5]dec-8-yl]acetamide hydrochloride Step A—Preparation of
4′,5′-Dihydro-7-methylspiro[7-azabicyclo[4.1.0]-heptane-3,2′(3H)-furan).

A mixture of cis-(±)-(1′α,3′β,6′α)-dihydrospirofuran-2(3H),3′-[7]-oxabicyclo[4.1.0]heptane and trans(±)-(1′α,3′β,6′α)-dihydrospirofuran-2(3H),3′-[7]oxabicyclo[4.1.0]heptane, prepared according to the method disclosed in U.S. Pat. No. 4,438,130, is slowly added with stirring to an ice-cold 25%-30% aqueous solution of methylamine (Aldrich Chemical Co. Milwaukee, WI, USA). The mixture is allowed to warm to room temperature and is stirred at ambient temperature overnight and then heated under reflux for three hours.

The mixture is cooled, saturated with sodium hydroxide and then extracted diethyl ether. The ether solution is dried over anhydrous magnesium sulfate, and the ether removed under vacuum to yield a crude mixture of 7-(methylamino)-1-oxaspiro[4.5]decan-8-ol and 8-(methylamino)-1-oxaspiro[4.5]decan-7-ol.

The mixture of amino-alcohols is dissolved in diethyl ether and cooled in an ice-salt bath. Chlorosulfonic acid is added dropwise with stirring over a period of one hour. The mixture is allowed to warm to room temperature, and then stand for three hours. The ether is decanted, and the residual white salt is washed with ether. The salt is cooled in an ice bath, and aqueous sodium hydroxide is slowly added.

The crude 4′,5′-dihydro-7-methyl-spiro[7-azabicyclo[4.1.0]heptane-3,2′(3′H)-furan is purified by recrystallization.

Step B—Preparation of
1-[8-(methylamino)]-1-oxaspiro[4.5]dec-7-yl]pyrrolidine

4′,5′-Dihydro-7-methyl-spiro[7-azabicyclo[4.1.0]heptane-3,2′(3′H)-furan (0.06 mol), prepared as described in Step A above, is mixed with 0.25 mol of pyrrolidine, 10 ml of water and 0.16 g of ammonium chloride. The mixture is heated under reflux for 20 hours and then cooled to room temperature. Solid sodium hydroxide is added, and the basic mixture is extracted with diethyl ether. The ether extract is dried over anhydrous magnesium sulfate, and the either is removed under vacuum. The mixture of (5α,7α,8β)-1-[8-(methylamino)]-1-oxaspiro[4.5]dec-7-yl]pyrrolidine and (5α,7β,8α)-1-[8-(methylamino)]-1-oxaspiro[4.5]dec-7-yl]pyrrolidine is separated by chromatography to yield the desired pure (5α,7α,8β)-1-[8-(methylamino)]-1-oxaspiro[4.5]dec-7-yl]pyrrolidine.

Step C—Preparation of
2-(3,4-Dichlorophenoxy-N-methyl-[7-(1-pyrrolidinyl)-1-oxaspiro[4.5]dec-8-yl]acetamide 1-[8-(Methylamino)]-1-oxaspiro[4.5]dec-7-yl]pyrrolidine, prepared as described in Step B above, is dissolved in methylene chloride. To the stirred solution is added, at room temperature, a mixture of 3,4-dichlorophenoxy acetyl chloride and triethylamine. The mixture is allowed to stand at room temperature for about 12 hours, and ether is added to crystallize the product, mp 188°–198° C.

The infrared spectrum (neat on NaCl disk) exhibited principal absorption peaks at 1651 and 1590 reciprocal centimeters.

The 300 MHz proton magnetic resonance spectrum of a deuterochloroform solution of the compound exhibited signals at 11.5 (broad singlet, 1H); 7.29 (multiplet, 2H); 7.06 (doublet of doublets, J=9.3 Hz, 1H); 5.31 (broad doublet, J=14 Hz, 1H); 4.82 (doublet, J=14 Hz, 1H); 4.20 (broad singlet), 1H); 3.94 (broad singlet, 1H); 3.85 (multiplet, 2H); 3.55 (broad singlet, 1H); 3.35 (broad singlet, 1H); 3.06 (singlet, 3H); 3.01 (broad singlet, 2H); and 2.4–1.5 (multiplet, 14H) parts per million downfield from tetramethylsilane.

EXAMPLE 2

Preparation of
N-Methyl-2-(1-naphthalenyloxy)-N-[7-(1-pyrrolidinyl)-1-oxaspiro[4.5]dec-8-yl]acetamide Step A—Preparation of 1-Naphthalenyloxyacetyl Chloride 1-Naphthalenyloxyacetic acid (Shibata et al. *Tech. Repts. Tohoku Imp. Univ.*, 12: 119–135 (1936) is heated with thionyl chloride under reflux until no further solid remains. The mixture is cooled and the excess thionyl chloride is removed under vacuum. Any additional thionyl chloride remaining after this treatment is removed by azeotropic distillation with carbon tetrachloride.

Step B—Preparation of
N-Methyl-1-(1-naphthalenyloxy-N-[7-(1-pyrrolidinyl)-1-oxaspiro[4.5]dec-8-yl]acetamide The naphthalenyloxyacetyl chloride from Step A is dissolved in a 1:1 mixture of diethyl ether and dichloromethane and an ethereal solution of 1-[8-(methylamino)]-1-oxaspiro[4.5]dec-7-yl]pyrrolidine (prepared as described in Example 1, Step B above) is added dropwise with stirring.

The resulting mixture is stirred for one-half hour at room temperature and then cooled to 0° C. and diethyl ether is added until no further precipitate forms. This mixture is stirred for an additional 15 minutes and the precipitated N-methyl-2-(1-naphthalenyloxy)-N-[7-(1-pyrrolidinyl)-1-oxaspiro[4.5]dec-8-yl]acetamide monohydrochloride salt is collected by filtration and purified by recrystallization, mp 230°–232° C.

The 300 MHz proton magnetic resonance spectrum of a hexadeutero-dimethylsulfoxide solution of the product exhibited signals at about 1.75 (multiplet, 14H); 2.98 (singlet, 3H); and about 3.3 (multiplet obscured by water signal); 4.55 (multiplet, 1H); 5.16 (doublet of doublets, 2H); about 7.7 (multiplet, 7H), and 10.0 (broad singlet, 1H) parts per million downfield from tetramethylsilane.

EXAMPLE 3

Preparation of
N-Methyl-N-[7-(1-pyrrolidinyl)-1-oxaspiro[4.5]dec-8-yl]-3-indeneacetamide Employing the general methods detailed above the title compound was prepared as the monohydrochloride salt, mp 121°–124° C.

The infrared spectrum of the compound (neat on an NaCl disk) showed a principal absorption peak at 1642 reciprocal centimeters.

The 300 MHz proton magnetic resonance spectrum of a deuterochloroform solution of the compound exhibited signals at 11.5 (broad singlet, 1H); 7.51 (doublet, J=7 Hz, 1H); 7.43 (doublet, J=7 Hz, 1H); 7.25 (multiplet, 2H); 6.34 (singlet, 1H); 4.75 (broad singlet, 1H); 3.90 (singlet, 2H); 3.85 (multiplet, 3H); 3.65 (broad singlet, 1H); 3.42 (multiplet, 1H); 3.38 (singlet, 2H); 3.12 (singlet, 3H), 2.97 (broad singlet, 2H), and 2.3–1.5 (multiplet, 14H) parts per million downfield from tetramethylsilane.

EXAMPLE 4

Preparation of
N-Methyl-N-[7-(1-pyrrolidinyl)-1-oxaspiro[4.5]dec-8-yl]-4-indoleacetamide Employing the general methods detailed above the title compound was prepared, mp 199°–202° C.

The infrared spectrum of a dichloromethane solution of the compound exhibited a principal absorption peak at 1625 reciprocal centimeters.

The 300 MHz proton magnetic resonance spectrum of a deuterochloroform solution of the compound exhibited signals at 8.3 (broad singlet, 1H); 6.7–7.4 (multiplet), 5H); 3.7–4.1 (multiplet, 6H), 2.5–3.0 (multiplet, 6H); and 1.5–2.1 (multiplet, 12H) parts per million downfield from tetramethylsilane.

EXAMPLE 5

Preparation of
N-Methyl-N-[7-(1-pyrrolidinyl)-1-oxaspiro[4.5]dec-8-yl]-2-benzo[b]furanacetamide Employing the general methods detailed above the title compound was prepared as the monohydrochloride salt, mp 187°–190° C.

The 300 MHz proton magnetic resonance spectrum of a hexadeutero-dimethylsulfoxide solution of the compound exhibited signals at about 1.75 (multiplet, 14H); 2.99 (singlet, 3H); about 3.35 (multiplet, signal obscured by water signal); 4.05 (doublet of doublets, 2H); 4.58 (multiplet, 1H); about 7.55 (multiplet, 5H); and 10.0 (broad singlet, 1H) parts per million downfield from tetramethylsilane.

EXAMPLE 6

Preparation of
2-(3,5-Dichlorophenoxy)-N-[7-(1-pyrrolidinyl)amino]-1-oxaspiro[4.5]dec-8-yl]acetamide Employing the general methods detailed above the title compound was prepared as the monohydrochloride salt, mp 122°–124° C.

The 300 MHz proton magnetic resonance spectrum of a hexadeutero-dimethylsulfoxide solution of the compound exhibited signals at about 1.75 (multiplet, 14H); 2.91 (singlet, 3H); about 3.4 (multiplet, signal obscured by water signal); 4.55 (multiplet, 1H); 5.10 (doublet of doublets, 2H); 7.08 (triplet, 1H); 7.2 (doublet, 2H); and 10.2 (broad single, 1H) parts per million downfield from tetramethylsilane.

EXAMPLE 7

Preparation of
N-Methyl-N-[7-(1-pyrrolidinyl)-1-oxaspiro[4.5]dec-8-yl]-2-(3-trifluoromethylphenoxy)acetamide Employing the general methods detailed above the title compound was prepared as the monohydrochloride salt, mp 176°–179° C.

The 300 MHz proton magnetic resonance spectrum of a hexadeutero-dimethylsulfoxide solution of the compound exhibited signals at about 1.75 (multiplet, 14H); 2.92 (singlet, 3H); about 3.3 (multiplet, signal obscured by water signal); 4.55 (multiplet, 1H); 5.08 (doublet of doublets, 2H); about 7.3 (multiplet, 4H); and 9.9 (broad singlet, 1H) parts per million downfield from tetramethylsilane.

EXAMPLE 8

Preparation of
2-(4-Fluorophenoxy)-N-[7-(1-pyrrolidinyl)amino]-1-oxaspiro[4.5]dec-8-yl]acetamide Employing the general methods detailed above the title compound was prepared as the monohydrochloride salt, mp 184° C.

The 300 MHz proton magnetic resonance spectrum of a hexadeutero-dimethylsulfoxide solution of the compound exhibited signals at about 1.75 (multiplet, 14H); 2.89 (singlet, 3H); about 3.3 (multiplet, signal obscured by water signal); 4.55 (multiplet, 1H); 4.88 (doublet of doublets, 2H); about 7.05 (multiplet, 4H); and about 9.8 (broad singlet, 1H) parts per million downfield from tetramethylsilane.

EXAMPLE 9

Preparation of
N-Methyl-N-[7-(1-pyrrolidinyl)-1-oxaspiro[4.5]dec-8-yl]-2-(3-nitrophenoxy)acetamide Employing the general methods detailed above the title compound was prepared as the monohydrochloride salt, mp 105°–110° C.

The 300 MHz proton magnetic resonance spectrum of a hexadeutero-dimethylsulfoxide solution of the compound exhibited signals at about 1.75 (multiplet, 14H); 2.92 (singlet, 3H); about 3.3 (multiplet, signal obscured by water signal); 4.55 (multiplet, 1H); 5.11 (doublet of doublets, 2H); about 7.52 (multiplet, 2H); 7.81 (multiplet, 2H); and 9.9 (broad singlet, 1H) parts per million downfield from tetramethylsilane.

EXAMPLE 10

Preparation of
N-Methyl-[7-(1-pyrrolidinyl)-1-oxaspiro[4.5]dec-8-yl]-4-benzo[b]thiopheneacetamide Employing the general methods detailed above the title compound was prepared as the monohydrochloride salt, mp 231°–234° C.

The 300 MHz proton magnetic resonance spectrum of a hexadeutero-dimethylsulfoxide solution of the compound exhibited signals at about 1.75 (multiplet, 14H); 3.02 (singlet, 3H); about 3.3 (multiplet, signal obscured by water signal); 4.18 (doublet of doublets, 2H); 4.55 (multiplet, 1H); 7.5 (multiplet, 5H); and about 10.1 (broad singlet, 1H) parts per million downfield from tetramethylsilane.

EXAMPLE 11

Preparation of
N-Methyl-N-[7-(1-pyrrolidinyl)-1-oxapsiro[4.5]dec-8-yl]-2-(3,4,5-trimethylphenoxy)acetamide Employing the general methods detailed above the title compound was prepared as the monohydrochloride salt, mp 214°–217° C.

The 300 MHz proton magnetic resonance spectrum of a hexadeutero-dimethylsulfoxide solution of the compound exhibited signals at about 1.75 (multiplet, 14H); 2.01 (singlet, 3H); 2.18 (singlet, 6H): 2.93 (singlet, 3H); about 3.3 (signal obscured by water signal); 4.55 (multiplet, 1H); 4.85 (doublet of doublets, 2H); 6.70 (singlet, 2H); and 10.3 (broad singlet, 1H) parts per million downfield from tetramethylsilane.

I claim:

1. A compound having the structure

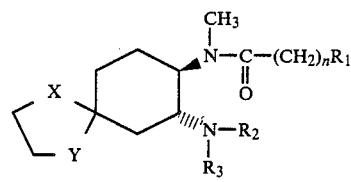

wherein n is an integer of from one to six; either of X or Y is oxygen and the other is —CH$_2$—;

R$_1$ is selected from

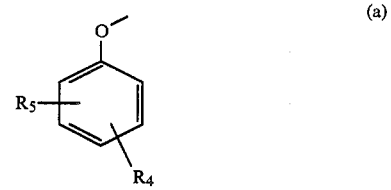

(a)

where R$_4$ and R$_5$ are independently hydrogen, fluorine, chlorine, bromine, nitro, trifluoromethyl, alkyl of from one to six carbon atoms, alkoxy of from one to six carbon atoms, or aryl;

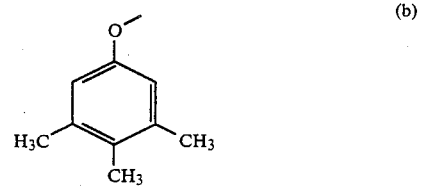

(b)

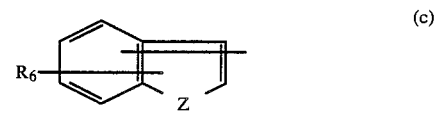

(c)

where R$_6$ is hydrogen, fluorine, chlorine, alkyl of from one to six carbon atoms, or aryl; Z is —CH$_2$—, —O—, —S—, or —NR$_7$— where R$_7$ is hydrogen, alkanoyl of from two to six carbon atoms, or alkyl of from one to six carbon atoms;

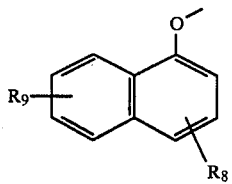

where $R_8$ and $R^9$ are independently hydrogen, fluorine, chlorine, bromine, alkyl of from one to six carbon atoms, or alkoxy of from one to four carbon atoms; or (e) 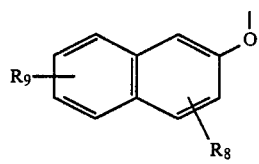

where $R_8$ and $R_9$ are as defined above;
$R_2$ is methyl and $R_3$ is hydrogen; alkyl of from one to six carbon atoms,;

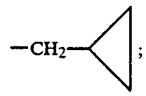

$-CH_2-CH=CH_2$, $-CH_2C\equiv CH$;

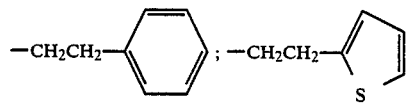

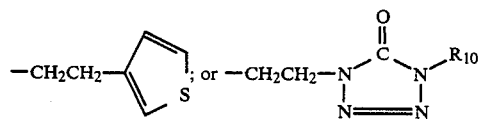

where $R_{10}$ is alkyl of from one to four carbon atoms; or where $R_2$ and $R_3$ when taken together with the nitrogen atom to which they are attached, form a pyrrolidinyl, piperidinyl, or hexahydro-1H-azepinyl ring;
   and the pharmaceutically acceptable acid addition salts thereof.

2. A compound as defined in claim 1 wherein n is one.

3. A compound as defined in claim 1 wherein $R_2$ and $R_3$ taken together with the nitrogen atom to which they are attached form a pyrrolidinyl ring.

4. A compound as defined in claim 1 wherein $R_1$ is

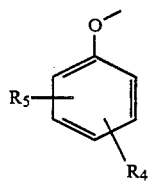

where $R_4$ and $R_5$ are as defined therein.

5. A compound as defined by claim 1 wherein

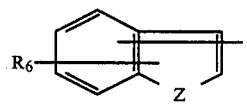

where $R_6$ and Z are as defined therein.

6. A compound as defined by claim 5 wherein Z is $-CH_2-$.

7. A compound as defined by claim 5 wherein Z is oxygen.

8. A compound as defined by claim 5 wherein Z is sulfur.

9. A compound as defined by claim 5 wherein Z is $-NR_7-$ where $R_7$ is as defined therein.

10. A compound as defined by claim 1 wherein $R_1$ is

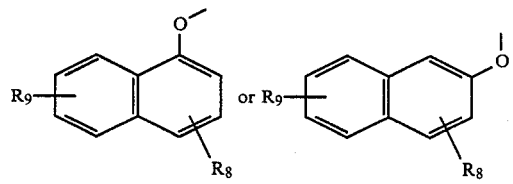

where $R_8$ and $R_9$ are as defined therein.

11. A compound as defined by claim 4 having the name N-methyl-N-[7-(methyl-2-propynylamino)-1-oxaspiro[4.5]dec-8-yl]phenoxyacetamide.

12. A compound as defined by claim 7 having the name N-[7-[(cyclopropylmethyl)methylamino]-1-oxaspiro[4.5]dec-8-yl]-N,2-dimethylbenzo[b]furan-3-acetamide.

13. A compound as defined by claim 9 having the name N-methyl-N-[7-(1-pyrrolidinyl)-1-oxaspiro[4.5]-dec-8-yl]-1H-indole-3-acetamide.

14. A compound as defined by claim 4 having the name N-methyl-N-[7-(1-pyrrolidinyl)-1-oxaspiro[4.5]-dec-8-yl]-2-(3-nitrophenoxy)acetamide.

15. A compound as defined by claim 4 having the name N-methyl-N-[7-(1-pyrrolidinyl)-1-oxaspiro[4.5]-dec-8-yl]-2-(3-trifluoromethylphenoxy)acetamide.

16. A compound as defined by claim 7 having the name N-methyl-N-[7[(1-pyrrolidinyl)-1-oxaspiro[4.5]-dec-8-yl]-2-bemzo[b]furanacetamide.

17. A compound as defined by claim 7 having the name N-methyl-N-[7[(1-pyrrolidinyl)-1-oxaspiro[4.5]-dec-8-yl]-3-bemzo[b]furanacetamide.

18. A compound as defined by claim 7 having the name N-methyl-N-[7[(1-pyrrolidinyl)-1-oxaspiro[4.5]-dec-8-yl]-4-bemzo[b]furanacetamide.

19. A compound as defined by claim 6 having the name N-methyl-N-[7-(methyl-2-propenylamino)-1-oxaspiro[4.5]dec-8-yl]-1H-indene-3-acetamide.

20. A compound as defined by claim 4 having the name 2-(4-fluorophenoxy)-N-methyl-N-[7-[methyl-(2-phenylethyl)amino]-1-oxaspiro[4.5]dec-8-yl]acetamide.

21. A compound as defined by claim 4 having the name 2-(3,4-dichlorophenoxy)-N-methyl-N-[7-(1-pyrrolidinyl)-1-oxaspiro[4.5]dec-8-yl]acetamide.

22. A compound as defined by claim 4 having the name 2-(2,6-dichlorophenoxy)-N-methyl-N-[7-(-1-pyrrolidinyl)-1-oxaspiro[4.5]dec-8-yl]acetamide.

23. A compound as defined by claim 4 having the name 2-(3,5-dichlorophenoxy)-N-methyl-N-[7-(1-pyrrolidinyl)-1-oxaspiro[4.5]dec-8-yl]acetamide.

24. A compound as defined by claim 6 having the name N-methyl-N-[7-(1-pyrrolodinyl)-1-oxaspiro[4.5]dec-8-yl]-3-indeneacetamide.

25. A compound as defined by claim 9 having the name N-[7-(dimethylamino)-1-oxaspiro-[4.5]dec-8-yl]-N-methyl-1H-indole-3-acetamide.

26. A compound as defined by claim 4 having the name 2-(4-fluorophenoxy)-N-methyl-N-[7-(1-pyrrolidinyl)-1-oxaspiro[4.5]dec-8-yl]acetamide.

27. A compound as defined by claim 10 having the name N-methyl-2-(1-naphthalenyloxy)-N-[7-(1-pyrrolidinyl)-1-oxaspiro[4.5]dec-8-yl]acetamide.

28. A method of alleviating pain in a warm-blooded animal comprising administering to said animal in need of such treatment an analgesically effective amount of a compound as defined by claim 1 in combination with a pharmaceutically acceptable carrier.

29. A compound as defined by claim 10 having the name N-methyl-N-[7-[methyl[2-(2-thienyl)ethyl]amino]-1-oxaspiro[4.5]dec-8-yl]-2-(1-naphthalenyloxy)acetamide.

30. A pharmaceutical composition useful for treating pain in a warm-blooded animal comprising an analgesically effective amount of a compound as defined by claim 1 in combination with a pharmaceutically acceptable carrier.

* * * * *